(12) United States Patent

Liu et al.

(10) Patent No.: US 6,465,009 B1
(45) Date of Patent: Oct. 15, 2002

(54) WATER SOLUBLE POLYMER-BASED RAPIDLY DISSOLVING TABLETS AND PRODUCTION PROCESSES THEREOF

(75) Inventors: Fang-yu Liu; Min Michael He; Janaki Ram Nyshadham; Kuldeepak Sharma, all of Fremont; James Shunnan Chu, Palo Alto; Joseph A. Fix, Half Moon Bay, all of CA (US)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/044,302

(22) Filed: Mar. 18, 1998

(51) Int. Cl.$^7$ .................................................. A61K 9/20
(52) U.S. Cl. ...................... 424/464; 424/439; 424/465; 424/470; 424/488; 514/772
(58) Field of Search ................................ 424/464, 439, 424/480, 465, 470; 514/772

(56) References Cited

U.S. PATENT DOCUMENTS

| | | | | |
|---|---|---|---|---|
| 4,371,516 | A | 2/1983 | Gregory et al. ................ | 424/22 |
| 4,572,832 | A | 2/1986 | Kigasawa et al. ............. | 424/19 |
| 4,684,534 | A | 8/1987 | Valentine ......................... | 427/3 |
| 4,764,378 | A | 8/1988 | Keith et al. .................. | 424/435 |
| 4,832,956 | A | * 5/1989 | Gergely et al. .............. | 424/466 |
| 5,039,540 | A | 8/1991 | Ecanow ....................... | 426/385 |
| 5,135,752 | A | 8/1992 | Snipes ........................ | 424/435 |
| 5,262,171 | A | 11/1993 | Login et al. ................. | 424/465 |
| 5,456,919 | A | * 10/1995 | Patell et al. ................. | 424/451 |
| 5,464,632 | A | 11/1995 | Cousin et al. ............... | 424/465 |
| 5,501,861 | A | 3/1996 | Makino et al. .............. | 424/464 |
| 5,506,248 | A | 4/1996 | Nikfor et al. ................ | 514/374 |
| 5,560,927 | A | 10/1996 | Menon et al. ............... | 424/464 |
| 5,576,014 | A | 11/1996 | Mizumoto et al. .......... | 424/435 |
| 5,622,719 | A | 4/1997 | Myers et al. ................ | 424/488 |
| 5,641,536 | A | 6/1997 | Lech et al. ................. | 427/2.14 |
| 5,650,169 | A | 7/1997 | Conte et al. ................. | 424/472 |
| 5,672,364 | A | 9/1997 | Kato et al. ..................... | 425/89 |
| 5,672,589 | A | 9/1997 | Heikkila et al. ............... | 514/53 |
| 5,684,121 | A | 11/1997 | Narayanan .................. | 528/363 |
| 6,024,981 | A | 2/2000 | Khankari et al. ........... | 424/464 |

FOREIGN PATENT DOCUMENTS

| | | | | |
|---|---|---|---|---|
| EP | 0 745 382 A1 | 1/1995 | ............ | A61K/9/20 |
| JP | Hei 08-291051 | 11/1996 | | |
| JP | 09-48726 | 2/1997 | | |
| WO | WO 97/12603 | 4/1997 | ............ | A61K/9/20 |

OTHER PUBLICATIONS

Asker AF, et al. Investigation of some materials as dry binders for direct compression in tablet manufacture. Part 2: Comparative self–binding properties. Pharmazie. Apr. 1, 1975; 30(4):236–238.
Asker AF, et al. Investigation of some materials as dry binders for direct compression in table manufacture. Part 6: Effect of drug. Pharmazie. Jul. 1, 1975; 30(7): 463–465.
Asker AF, et al. Investigation of some materials as dry binders for direct compression in tablet manufacture. Part 7: Formulation and evaluation of ascorbic acid and phenobarbitone tablets. Pharmazie. Jul. 1, 1975; 30(7): 466–470.
Bi Y, et al. Preparation and evaluation of a compressed tablet rapidly disintegrating in the oral cavity. Chem Pharm Bull (Tokyo). Nov. 1, 1996; 44(11): 2121–2127.
Chowhan ZT. Role of binders in moisture–induced hardness increase in compressed tablets and its effect on in vitro disintegration and dissolution. J Pharm Sci. Jan. 1, 1980; 69(1): 1–4.
Chowhan ZT, et al. Effect of moisture and crushing strength on tablet friability and in vitro dissolution. J Pharm Sci. Dec. 1, 1982; 71(12): 1371–1375.
De Jong JA. Relations between tablet properties. Pharm Weekbl [Sci]. Feb. 20. 1987; 9(1): 24–28.
Ghanta SR. et al. Some studies of the effect of processing variables on the properties of granules and tablets made by wet granulation. Pharm Acta Helv. Jan. 1, 1986; 61(7): 191–197.
Ibrahim HG. Observations on the dissolution behavior of a tablet formulation: effect of compression forces. J Pharm Sci. May 1, 1985; 74(5): 575–577.
Kawashima Y, et al. Low–substituted hydroxypropylcellulose as a sustained–drug release matrix base or disintegrant depending on its particle size and loading in formulation. Pharm Res. Mar. 1, 1993; 10(3): 351–355.
Khattab I, et al. Effect of mode incorporation of disintegrants on the characteristics of fluid–bed wet–granulated tablets. J Pharm Pharmacol. Aug. 1, 1993; 45(8): 687–691.
Kopp S, et al. Methodology for a better evaluation of the relation between mechanical strength of solids and polymorphic form. J Pharm Pharmacol. Feb. 1, 1989; 41(2): 79–82.
Lipps DM, et al. Characterization of wet granulation process parameters using response surface methodology. 1. Top–spray fluidized bed. J Phar Sci. Jul. 1, 1994; 83(7): 937–947.
Mukherjee In vivo cytogenetic studies on mice exposed to acesulfame–K–13 a non–nutritive sweetener. (1997) *Food Chem. Toxicol.* 35:1177–1179.
Nakagami H, et al. The use of micronized cellulose disintegrants as insoluble swellable matrices for sustained–release tablets. Drug Des Deliv. Jul. 1, 1991; 7(4): 321–332.
Rolls (1991) Effects of intense sweeteners on hunger, food intake, and body weight: a review. Am. J. Clin. Nutr. 53:872–878.

(List continued on next page.)

Primary Examiner—Thurman K. Page
Assistant Examiner—Latshmi Channavajjala
(74) Attorney, Agent, or Firm—Townsend and Townsend and Crew, LLP

(57) ABSTRACT

The invention provides for novel compressed tablets capable of rapidly disintegrating in aqueous solutions, comprising at least one non-saccharide water soluble polymer, which are free of organic solvent residues, and methods of making such pharmaceuticals.

24 Claims, No Drawings

OTHER PUBLICATIONS

Stafford JW, et al. Temperature dependence of the disintegration times of compressed tablets containing hydroxypropylcellulose as binder. J Pharm Pharmacol. Jan. 1, 1978; 30(1): 1–5.

Tanaka M, et al. Interaction between drugs and water-soluble polymers. I. Binding of warfarin and 4-hydroxycoumarin with polyvinylpyrrolidone and acrylamide–vinylpyrrolidone copolymer. Chem Pharm Bull (Tokyo). Dec. 1, 1988; 36(12): 4645–4651.

Vadas EB. et al. Effect of compressional force on tablets containing cellulosic disintegrators I: Dimensionless disintegration values. J Pharm Sci. Jun. 1, 1984; 73(6): 781–783.

van Velthuijsen Food additives derived from lactose: lactitol and lactitol palmitate. JA J Agric Food Chem Jul.–Aug. 1979;27(4):680–6.

Vojnovic D, et al. Formulation and evaluation of vinylpyrrolidone/vinylacetate copolymer microspheres with griseofulvin. J. Microencapsul. Jan. 1, 1993; 10(1): 89–99.

Watanabe Y, et al. New compressed tablet rapidly disintegrating in saliva in the mouth using crystalline cellulose and a disintegrant. Biol Pharm Bull. Sep. 1, 1995; 18(9): 1308–1310.

* cited by examiner

WATER SOLUBLE POLYMER-BASED RAPIDLY DISSOLVING TABLETS AND PRODUCTION PROCESSES THEREOF

FIELD OF THE INVENTION

This invention pertains to the field of pharmaceuticals, compressed tablet formulations and methods of manufacturing tablets.

BACKGROUND OF THE INVENTION

Pharmaceutically active agents are commonly formulated as solid tablets for oral administration due to reasons of stability, economy, simplicity and convenience of dosing. However, many patients cannot or will not accept tablet administration. Infants, children, individuals suffering from certain injuries or illnesses, and many elderly and disabled individuals cannot swallow or chew sufficiently to effectively administer a pharmaceutically active agent by means of a solid tablet. An effective means for oral administration of pharmaceutically active agents to these individuals would be highly beneficial. While liquid formulations can address this need in some cases, the technical complexities of liquid formulations and difficulties in patient compliance and ease of administration make liquid formulations a less than optimal approach. Thus, there is a great need to develop solid oral tablets which can be administered to this patient population. In these individuals, if a solid tablet is used to administer a pharmaceutically active agent, the ability of that preparation to rapidly disintegrate upon contact with the mucous membrane, such as the buccal cavity or sublingual area of the mouth, and deliver a therapeutically effective dose of the drug would be a major advantage. Furthermore, in many circumstances, it is important to have a fast disintegrating tablet so that the pharmaceutically active ingredient is absorbed as rapidly as possible.

However, manufacture of a tablet that is capable of such rapid disintegration typically results in a product which is too soft or friable to withstand packaging, shipping, and handling by the patient. Most attempts at producing a tablet capable of rapid disintegration in a body cavity, yet hard enough to not break up during packaging, shipping, and handling, have resulted in manufacturing processes that are complex and expensive.

Furthermore, many tablet manufacturing processes use organic solvents, thereby leaving unwanted and undesirable organic solvent residues in the final tablet formulation.

Thus, there exists a need for compressed tablets which are sufficiently hard to be packaged and handled by patients yet able to rapidly disintegrate in an aqueous environment similar to that found in a body cavity (e.g., oral cavity) and which does not require the additional ingestion of fluids for the purposes of swallowing a solid tablet. It would further be advantageous if such tablets could be made relatively economically, without the use of organic solvents. The present invention fulfills these and other needs.

SUMMARY OF THE INVENTION

This invention advantageously provides for tablets that are uniform in formulation and economical to produce. The formulation and method of manufacture of these compressed tablets surprisingly results in a tablet that is hard, and resistant to breakage during handling. Though the tablets are advantageously hard, they also rapidly disintegrate when they are contacted by body fluid or other aqueous medium. The tablets described here also have a greatly improved tactile effect making the tablets significantly more palatable to the consumer than other so-called rapidly dissolving tablets.

The invention provides a physiologically acceptable tablet comprising a compressed tablet formulation free of organic solvent residue that rapidly disintegrates when placed in a body cavity, that comprises at least one water soluble non-saccharide polymer, and that has a hardness factor of between about 0.5 kilopounds to about 12.0 kilopounds. The compressed tablet can have a hardness factor of over 6 kilopounds.

In various embodiments, the non-saccharide, water soluble polymer can be polyvinylpyrrolidone (PVP), polyethylene glycol, sodium alginate, hydroxypropyl cellulose, hydroxypropylmethyl cellulose, or hydroxyethyl cellulose. The non-saccharide, water soluble polymer can be between about 0.5% to about 20% of the dry weight of the tablet.

The PVP can be N-vinyl pyrrolidone, 3-methyl N-vinylpyrrolidone, N-vinyl amide pyrrolidone, N-vinyl acetate pyrrolidone, vinylpyrrolidone-vinyl acetate copolymer, and acrylamide- vinylpyrrolidone co-polymer. The PVP can have a molecular weight (MW) of less than about three million daltons, can have a MW of less than about fifty thousand daltons, or can have a MW of about thirty thousand daltons. The PVP can be about 5% of the dry weight of the tablet.

In one embodiment, the tablet of the invention is a formulation that further comprises a saccharide of low moldability. The low moldable saccharide can be mannitol, lactose, glucose, sucrose, lactitol, or a mixture thereof. The saccharide of low moldability can be between about 25% to about 99% of the weight of the tablet.

The formulation can also comprise a saccharide of high moldability, with the proviso that the formulation does not contain starch. The saccharide of high moldability can be maltose, maltitol, sorbitol, or a mixture thereof. The saccharide of high moldability can be about 0.5% to about 20% of the tablet.

The invention also provides a tablet further comprising a pharmaceutically active ingredient. The formulation of the invention can further comprise at least one additive agent selected from the group consisting of a disintegrant, a flavorant, an artificial sweetener, a perfume, and a colorant.

In various embodiments, the tablet of the invention dissolves in about 1 to about 40 seconds in an aqueous solution, the tablet dissolves in the oral cavity and the aqueous solution is saliva. The pharmaceutical tablet of the invention is suitable for delivery to a body cavity, such as, for example, the oral, buccal, sublingual, vaginal, nasal, rectal (anal), or urethral cavity.

The invention provides a process for producing a pharmaceutical tablet, comprising the following steps: (a) granulating a formulation comprising at least one non-saccharide, water soluble polymer and at least one active ingredient together, wherein no organic solvents are included in the formulation; (b) compressing the product of the granulation into a tablet form; (c) humidifying the tablet by exposing the product of step (b) to an aerated environment at least about 50% to 100% relative humidity; and (d) drying the tablet, wherein the hardness of the tablet is at least about 6 kilopounds. In various embodiments, the water soluble polymer comprises a PVP; the PVP can have a MW of less than about three million daltons, can have a MW of less than about fifty thousand daltons, or can have a MW of about thirty thousand daltons; the PVP can be about 5% of the dry weight of the formulation. The PVP of the process can be selected from the group consisting of N-vinyl pyrrolidone, 3-methyl N-vinylpyrrolidone, N-vinyl amide pyrrolidone, N-vinyl acetate pyrrolidone, vinylpyrrolidone-vinyl acetate copolymer, and acrylamide- vinylpyrrolidone co-polymer.

The process can include the addition of at least one lubricant and at least one filler to the tablet. In various embodiments, the lubricant can be in the range of about 0.5% to about 1.0% of the dry weight of the formulation, the lubricant in the formulation can be magnesium stearate or calcium stearate, the filler in the formulation can be in the range of about 80% to about 98% of the dry weight of the formulation, the filler in the formulation can be in the range of about 95% of the dry weight of the formulation, or the filler in the formulation can be mannitol.

In alternative embodiments of this process, in step (a) the temperature during granulation can range from about 10° C. to about 70°; in step (b) the compression can be by press molding; in step (b) the compression can produce a tablet with a hardness of about 0.3 to about 6.0 kilopounds; in step (c) the humidification can be between about 50% and about 100% relative humidity; in step (c) the humidification can be about 85% relative humidity; in step (c) the temperature can be at about 25° C.; in step (c) the humidification step can last for about 30 minutes or for about 60 minutes, resulting in a dried tablet with a hardness of about 4 kilopounds to about 5 kilopounds.

In another embodiment, step (c) of the process can have a humidification step that lasts for about 120 minutes, resulting in a dried tablet with a hardness of about 5 kilopounds to about 12 kilopounds, or a dried tablet with a hardness of about 7 kilopounds. In this process, step (d) can occur at a higher temperature and lower relative humidity than that of step (c). Step (d) can occur at a temperature of about 40° C. or can occur at a relative humidity of about 30%.

The invention also provides a tablet made by a process comprising the following steps: (a) granulating a formulation comprising at least one water soluble, non-saccharide polymer and at least one active ingredient together, wherein no organic solvents are included in the formulation; (b) compressing the product of the granulation into a tablet form; (c) humidifying the tablet by exposing the product of step (b) to an aerated environment at least about 50% to 100% relative humidity; and (d) drying the tablet, wherein the hardness of the dried tablet is about 0.5 kilopounds to about 12 kilopounds. The soluble polymer, non-saccharide polymer can be a PVP. In one embodiment, the PVP is about 5% of the dry weight of the formulation and the humidification step is about 60 minutes, resulting in a dried tablet with a hardness of about 4 kilopounds to about 5 kilopounds. In another embodiment, the PVP is at about 5% of the dry weight of the formulation and the humidification step is about 120 minutes, resulting in a dried tablet of about 5 kilopounds to about 12 kilopounds, or a dried tablet with a hardness of about 7 kilopounds.

A further understanding of the nature and advantages of the present invention may be realized by reference to the remaining portions of the specification, the figures and claims.

All publications, patents and patent applications cited herein are hereby expressly incorporated by reference for all purposes.

DETAILED DESCRIPTION OF THE INVENTION

The present invention provides for novel pharmaceutically acceptable tablets capable of rapidly disintegrating upon contact with a body cavity, as an oral mucous membrane. The tablets of the invention are free of organic solvent residues. They are also uniform in their formulation and of sufficient hardness such that they do not require an outer coating or layer to protect them from handling and shipping. Also provided are methods of making such tablets.

DEFINITIONS

The term "tablet" is used in its common context, and refers to a solid composition made by compressing and/or molding a mixture of compositions in a form convenient for swallowing or application to a body cavity.

The term "formulation" refers to any mixture of compositions used to make the tablets of the invention.

The term "body cavity" refers to any body cavity capable of receiving a tablet, including the oral, buccal, sublingual, eye, ear, vaginal, nasal, rectal, and urethral cavities.

The terms "organic solvent" and "organic solvent residue" are used in their common context, and include, e.g., alcohol, isopropyl alcohol, ethanol, methanol, methylene chloride, acetone, and the like.

The term "hardness factor" or "tablet hardness" refers to the tablet's "crushing" or "tensile" strength, and is defined as the force required to break a tablet by compression in the radial direction. It is typically measured using one of the many commonly available tablet hardness testers, see infra.

The term "water soluble polymer" refers to a polymeric composition, soluble in an aqueous solution, with a molecular weight of at least about 10,000 daltons.

The term "polyvinylpyrrolidone" or "PVP" refers to any of the polymers of vinylpyrrolidone, or derivatives thereof. While PVP is typically made by a free radical polymerization process, any soluble grade polymer of vinylpyrrolidone can be used in the compositions and methods of the invention. Typically, linear PVP polymers are water soluble and cross-linked PVP polymers are not water soluble.

The term "saccharide" refers to any monosaccharide or polysaccharide, or derivative thereof, from any natural or synthetic sources. The term "saccharide of low moldability" refers to a saccharide which shows a hardness of 0 to 2 kp when 150 mg of the saccharide is made into a tablet using a punch (die) of 8 mm in diameter under a pressure of 10 to 50 kg/cm$^2$, such as mannitol, lactose, glucose, sucrose, xylitol, and similar saccharides. The term "saccharide of high moldability" refers to a saccharide which shows a hardness of 2 kp or more when 150 mg of the saccharide is made into a tablet using a punch (die) of 8 mm in diameter under a pressure of 10 to 50 kg/cm$^2$, such as maltose, maltitol, sorbitol, oligosaccharides, and other similar saccharides, all defined in U.S. Pat. No. 5,576,014.

The term "friability" refers to a physical strength measurement of a compressed tablet, and is defined as the ability of the compressed tablet to resist abrasion and attrition. It is typically measured by turning tablets in a rotating vessel and determining weight loss, see infra.

The term "pharmaceutically active ingredient" refers to any medicament, nutritional, palliative, drug or pharmaceutical added to the tablet.

The term "disintegrant" refers to any composition which decreases the disintegration time (accelerates the rate of disintegration) of a tablet, as described infra.

The term "flavorant" refers to any composition which adds flavor to or masks the bad taste of a formulation. The term "artificial sweetener" refers to any synthetic composition that sweetens the taste of a formulation. The term "perfume" refers to any composition that contributes to the odor or taste, or masks an unpleasant smell, of a formulation. The term "colorant" refers to any composition that adds color to a formulation.

The term "granulating" refers to the process of blending and mixing a formulation in an aqueous solution, as described infra.

The term "compressing" refers to the process of applying compressive force to a formulation, as within a die, to form a tablet.

The term "humidifying" and "humidification" refer to the process of adding moisture to a tablet, as reacting the tablet with a relatively humid (water saturated) environment. The term "relative humidity" is used in its common context, and refers to the percentage of water saturation in a gas.

The term "drying" and "dried" refer to a process which decreases the water content of a composition, as the drying of a humidified tablet, as described infra. The term "dried tablet" refers to a tablet that has been treated in any manner to decrease the amount of water in the formulation, as when a tablet is dried after its initial granulation and compression into a tablet form.

The term "filler" refers to any inert material or composition added to a formulation to add bulk to a formulation.

The term "press molding" refers to any apparatus which places compressive force on a formulation to compress and shape the composition, as with the compression of a wet formulation to create a tablet.

The term "physiologically acceptable" refers to any combination of materials or compositions that are not harmful, i.e., non-toxic, to cells and tissues under physiologic (in vivo) conditions.

1. FORMULATION OF TABLETS

The invention provides for a tablet which, when placed in a body cavity, rapidly disintegrates without the need for any co-application or ingestion of fluid. For example, the tablets of the invention rapidly disintegrate in the oral cavity without requiring the need to intake a fluid. The ability to use a fast-disintegrating tablet without co-ingestion of water or other fluids allows for convenient administration of the tablet regardless of the age or condition of the individual, the time or the place. This property is especially suitable for use in infants, small children, the elderly, disabled, and the like. Furthermore, when the tablet is given orally, the rapid disintegration of the tablet can be an important factor in the effectiveness of the drug carried by the tablet. In some circumstances, the rapid disintegration enhances the action of the drug.

The rapidly disintegrating tablets of the invention disintegrate in about 1 second to about 40 seconds and have adequate hardness (more than about 0.5 Kg) to go through handling procedures during the manufacturing, packaging and distribution processes.

Moreover, the tablets of the invention are free of organic solvent residues. No organic solvents are used in the invention's manufacturing processes.

For the typical tablet, its formulation and manufacturing process are a tradeoff between two almost mutually exclusive properties: the ability to rapidly dissolve and hardness. Usually, when the ease of dissolution (i.e., the rapidity of disintegration) of the tablet is increased, the hardness of the tablet decreases. The invention provides a new formulation and manufacturing process that overcomes these previous limitations and that achieves the optimal balance between physical properties needed for manufacturing and handling, e.g., hardness, and rapid disintegration (dissolving) characteristics in vivo, in addition to other advantageous properties, such as being free of organic solvents and having an improved, smooth tactile effect ("mouth feel").

1. Water Soluble Polymers as Binders in Tablet Formulation

The tablet formulation of the invention comprises a binder having at least one water-soluble or water dispersible polymer that is not a saccharide. In alternative embodiments, the non-saccharide, water soluble polymer can be polyvinylpyrrolidone, polyethylene glycol, gelatin, agar, sodium alginate (alginic acid and derivatives), hydroxypropyl cellulose, hydroxypropylmethyl cellulose, hydroxyethyl cellulose, cellulose derivatives in general, carboxyvinyl polymers, glucans, mannans, xantan gums, and the like. The tablet can contain any combination of these water-soluble, polymer binders.

The binders used in these tablets can also contain a mixture of water soluble, non-saccharide polymer(s) with another binder, such as a saccharide of high moldability, e.g., maltose, maltitol, sorbitol, or a mixture thereof (saccharides of low moldability can be included in the tablet formulation as fillers, as discussed below).

In some embodiments, advantageous binder combinations can include a non-saccharide water soluble polymer and a saccharide having high moldability at a weight ratio of about 1:9 to about 9:1. The tablets of the invention are not limited by these ratios, and in some embodiments, they contain no saccharides of high moldability (saccharides of low moldability can also be optionally included in the tablet formulation, as discussed below).

Binders impart cohesiveness to the tablet and ensure tablet strength after compression. Water soluble binders are also important in the humidification step, discussed infra. The binder swells upon absorption of the water, allowing more thorough hydration of the other compositions of the formulation and deeper penetration of the water into the tablet. The non-saccharide, water soluble polymers also act as a disintegrant, contributing to the rapid disintegration properties of the tablets of the invention. The non-saccharide, water soluble polymers also contribute to and enhance the "smooth feeling" of the tablet when it dissolves in the mouth.

Polyvinylpyrrolidone ("PVP") is a preferred non-saccharide, water-soluble, polymer binder in the invention. In one embodiment, partial or complete replacement of the formulation's non-PVP water soluble polymer binder(s) by PVP allows a lower level of water insoluble lubricant, such as magnesium stearate, to be used in the formulation while retaining the properties of a "smooth feeling" when the tablet dissolves in the mouth. Use of PVP also provides for a quicker in vivo disintegration/dissolving time, as discussed infra.

Use of PVP as the only binder in the formulation results in tablets with a better resistance to moisture (i.e., the tablets absorb less moisture after manufacture). Use of PVP in lieu of saccharides in the formulation has the same advantage as when using other synthetic polymers versus materials from a natural source, i.e. lower contaminant levels and prices.

PVP can be any polymer of vinylpyrrolidone. PVP can be procured from a variety of commercial sources, such as, e.g., Povidone (supplied by BASF, Japan, with the trade name of Kollidon®) or Plasdone®(Gaf Corp., Wayne, N.Y.). In a preferred embodiment, the soluble Povidone Kollidone® 30 is used in the manufacture of the tablet (the value of 30, or K-value, indicates an average PVP molecular weight of 30,000 daltons). In alternative embodiments, the PVP can be N-vinyl pyrrolidone, 3-methyl N-vinylpyrrolidone, N-vinyl amide pyrrolidone, N-vinyl acetate pyrrolidone (copolyvidone, Kollidon VA64®, BASF, Japan), vinylpyrrolidone-vinyl acetate copolymer (Vojnovic (1993)

J. *Microencapulation* 10:89–99), acrylamide-vinylpyrrolidone co-polymer (GAF Italia; Tanaka (1988) *Chem. Pharm. Bull.* 36:4645–4651), or any PVP derivative thereof.

In various embodiments, the amount of PVP in the formulation is between about 0.5% to about 10% of the volume of the tablet. In one preferred embodiment PVP is about 5% of the volume. In one embodiment, PVP is used as the sole binder in a formulation, at a total of about 5% of the formulation. In alternative embodiments, PVP is used in varying amounts with at least one other binder, such as, e.g., a water soluble polymer such as polyethylene glycol, sodium alginate, hydroxypropyl cellulose, hydroxypropylmethyl cellulose, hydroxyethyl cellulose, or a saccharide of high moldability, e.g., maltose. Exemplary binder combinations include: about 0.5% of PVP and about 4.5% maltose; about 1.5% of PVP and about 3.5% maltose; about 2.5% of PVP and about 2.5% maltose; about 3.0% of PVP and about 2.0% maltose, or any other combination of maltose and PVP, or equivalent compositions, thereof.

The use of PVP as the only binder in a formulation, i.e., in lieu of a water soluble polymer or a saccharide of high moldibility, e.g., maltose, as binder in the manufacturing processes of the invention produces a tablet with significantly reduced friability. For example, when mannitol was granulated in a fluid bed granulator using 4.5% maltose and 0.5% PVP as binding agent, the resulting tablets showed a friability of 1.4%. When processed under identical conditions except using a binder solution of 5% PVP (no maltose), the friability of the resulting tablets was reduced to 0.7%. The significant reduction in tablet friability observed by replacing a maltose/PVP binder solution with a PVP only binder solution affords significant advantages in terms of tablet physical properties and integrity.

2. Saccharides of Low Moldability as Fillers in Tablet Formulation

The invention optionally provides for a tablet formulation comprising a single or a mixture of two saccharides of low moldability, such as mannitol, erythritol, xylitol, lactose, glucose, sucrose, lactitol, or other similar saccharides or derivatives thereof of low moldability, or a mixture thereof, as filler in the tablet formulation. In different embodiments, the saccharide of low moldability is about 40% to about 99% of the weight of the tablet, or is about 25% to about 98%.

3. No Organic Solvents Used in Tablet Formulation

Tablet manufacturing processes frequently use organic solvents, leaving an organic solvent residue in the final tablet product (see, e.g., Japanese Patent Application No. Hei 7-91083; Kigasawa, et al., U.S. Pat. No. 4,572,832; Gregory, et al., U.S. Pat. No. 4,371,516; Conte, et al., U.S. Pat. No. 5,560,169). The methods of the invention do not utilize organic solvent in the manufacturing process. This results in a finished tablet completely lacking in any organic solvent residue.

4. Other Formulation Components

In one embodiment, the tablets of the invention will optionally include an insoluble lubricant, such as magnesium stearate, or a derivative thereof. In various embodiments, the magnesium stearate is between 0.1% and 2.0%, or between 0.5% and 1.0%, of the weight of the tablet. Lubricants help in the manufacturing of the tablet; e.g., they help prevent "ejection sticking" of compressed formulation to the pressing dies and punches.

In another embodiment, a disintegrant other than the non-saccharide water soluble polmers described herein, such as PVP, is added to the formulation to further enhance the rate of disintegration. Disintegrants include, e.g., croscarmellose sodium, sodium starch glycolate, and the like; see, e.g., Khattab (1992) *J. Pharm. Pharnacol.* 45:687–691.

The tablets of the invention can further comprise any medicament, drug, palliative, nutritive, or pharmaceutically active material, e.g., a drug, medicament, nutrient, placebo, and the like, can be added to the formulation of the invention. However, the invention is broadly applicable to a wide variety of tablets including, but not limited to, tablets for, example, antacids, gastrointestinal agents, analgesics, antiinfectives, CNS-active agents, cardiovascular agents, cough therapies, vitamins, and other pharmaceutical, nutritional and dietary agents. In a preferred embodiment, fhe particle size of the medicament, drug, palliative, nutritive, or pharmaceutically active material is in such a range that the "mouth feel," or smooth tactile effect, of the final product (the tablet of the invention) in the oral cavity will not be negatively affected.

For a medicament, drug, palliative, nutritive, or pharmaceutically active material that has a bitter taste or stinging effect when given into the mouth, an extra taste-masking ingredient may be added to ensure the good clinical acceptance of the tablets (e.g., a spray dried peppermint flavor). Up to 50% (weight/weight) of coated active material can be included in the formulation. The particle size of the coated material should be less than 425 µm (#40 mesh). Colors, flavors and sweeteners can also be included in the formulation to improve the overall organoleptic characteristics of the final product.

Any colorant can be used, as long as it is approved and certified by the FDA. For example, exemplary colors include allura red, acid fuschin D, naphtalone red B, food orange 8, eosin Y, phyloxine B, erythrosine, natural red 4, carmine, to name a few. The most common method of adding color to a tablet formulation is to dissolve the dye in the binding solution prior to the granulating process.

In one embodiment, sweetening agents are added to the tablet formulation to create or add to the sweetness (which is afforded by the presence of saccharide fillers and binders, e.g., mannitol, lactose, and the like). For example, cyclamates, saccharin, aspartame, acesulfame K (Mukherjee (1997) *Food Chem. Toxicol.* 35:1177–1179), or the like (Rolls (1991) *Am. J. Clin. Nutr.* 53:872–878), can be used. Sweeteners other than sugars have the advantage of reducing the bulk volume of the tablet and not effecting the physical properties of the granulation.

In another embodiment, biodegradeable microspheres or capsules or other biodegradeable polymer configurations capable of sustained delivery of a composition (e.g., a pharmaceutical) (see, e.g., Putney (1998) *Nat. Biotechnol.* 16:153–157) can be included in the tablets of the invention. This allows for the advantageous combination of a rapidly distintegrating tablet (of the invention) releasing a second agent (the sustained delivery construction).

2. MANUFACTURING PROCESSES

The invention provides for a method of manufacturing the rapidly disintegrating tablet of the invention. The steps involved in the tablet's manufacture comprise a granulation (blending) step, a compression step, and two treatment steps—a humidification step and a drying step. All of these processing steps require no more than conventional processing equipment.

1. Granulation Step

The components of the tablet, as described above, including, e.g., a pharmaceutically active material, binder(s), filler(s), lubricant(s), etc., are blended, or granulated, in an aqueous solution. This blending process is commonly called "wet granulation." "Granulation" is commonly defined as a size-enlargement process in which small particles are gathered into larger, permanent aggregates in which the original particles can still be identified. "Wet granulation" is a variation on this process, as refers to a granulation that adds solvents and binders to the enlargement process. See, e.g., Lipps (1993) *J. Pharm. Sci.* 83:937–947.

A variety of such blending, or mixing, or granulating, apparatus are commonly available. For example, the granulation can be done on a Fluid Bed Granulator, such as the one designed by Glatt Air Techniques Inc., N.J.

The temperature during granulation can be set at any point as long as it does not exceed the melting point of any components in the formulation and the balance between spraying and drying is kept. Typically, the temperature is set in the range of 20° C. to 50° C.

2. Compression Step

The compression of the formulation after the granulation step can be accomplished using any tablet press, provided that the tablet composition is adequately lubricated. The level of lubricant in the formulation is typically in the range of 0.5–1.0%, with magnesium stearate most commonly used as a lubricant. Many alternative means to effect this step are available, and the invention is not limited by the use of any particular apparatus. In a preferred embodiment, the compression step is carried out using a rotary type tablet press. The rotary type tableting machine has a rotary board with multiple through-holes, or dies, for forming tablets. The formulation is inserted into the die and is subsequently press-molded.

The diameter and shape of the tablet depends on the die and punches selected for the compression of the granulation composition. Tablets can be discoid, oval, oblong, round, cylindrical, triangular, and the like. The tablets may be scored to facilitate breaking. The top or lower surface can be embossed or debossed with a symbol or letters.

The compression force can be selected based on the type/model of press, what physical properties are desired for the tablets product (e.g., desired, hardness, friability, in vivo disintegration or dissolution characteristics, etc.), the desired tablet appearance and size, and the like. The tablets from the compression stage typically have a hardness of about 0.3 to about 6 kp.

In a preferred embodiment, the amount of compressive force used is the least amount of force needed to produce a tablet form capable of being extruded from the die and the press-molding machine and transferred to the moisturizing/drying chamber. If the minimal amount of compressive force is used, it is expected that the tablet at this point in the manufacturing process is too soft to be packaged, shipped or handled by the consumer. However, as described below, the subsequent treatment steps will sufficiently harden the tablet to produce a product sufficiently hard to be packaged, shipped and handled without unacceptable amounts of loss of tablet integrity (as crushing, chipping, etc.) yet capable of rapid disintegration upon administration.

3. Humidification and Drying Steps

To provide for a tablet that is both rapidly disintegrating and has a relatively great strength (increased hardness), the method of the invention provides for a two-step treatment stage, which includes a humidification step and a drying step. Both treatments can be carried out in a single environmental chamber where both temperature and humidity can be accurately controlled. Many means to effect these steps are available, and the invention is not limited by the use of any particular apparatus.

The treatment condition of the humidification step should be set at a lower temperature and a higher moisture level (higher relative humidity) than the drying step. The desired final product properties can be achieved by routine testing and optimization of treatment conditions that are dependent on individual formulations, especially the amount or type of PVP in the tablet.

In the humidification step, the water-soluble polymer binder contained in the tablet-forming material swells upon absorption of the water, allowing more thorough wetting (hydration) of the other components of the formulation and deeper penetration of the wetting agent (water) into the tablet interior. In the drying process, the water is removed from the tablet. This loss of water by the binder in the drying process results in a harder tablet. Others have shown that a short humidification step (10 seconds to 30 minutes) followed by drying results in tablets with a relatively soft interior (as determined by the amount of force in the compression step) and a relatively harder outer (exterior) surface layer. The result is a tablet with a hardness sufficient to be further packaged, shipped and handled, yet still capable of rapidly disintegrating when placed in a body cavity. Surprisingly, in the invention disclosed here, even longer humidification times ($\geq 30$ minutes) with the instant formulation affords uniform hardness throughout the tablet and provides for a tablet with improved hardness which still maintains a rapid disintegration time.

In different embodiments, the relative humidity (RH) in the humidification step is between about 50% and 100%; the humidification step lasts for between about 5 minutes to about 12 hours; and the temperature at which the humidification step is carried out can be between about 20 minutes to about 50 minutes. In preferred embodiments, for tablets formulated using 95% mannitol as filler and 5% maltose as binding agent: humidification can be at 25° C. at 85% RH for 30 minutes, followed by drying at 40° C. at 30% RH for 30 minutes. These treatment conditions can also be applied to batches using 0.5% PVP and 4.5% maltose solution as binders.

In embodiments where 5% PVP solution is used as the only binder agent (i.e., no maltose or other saccharide); the humidification time is preferably increased to about 60 to about 120 minutes. Different drying conditions can be used to achieve desired tablet hardness, which is measured after the tablet is dried. For example, with a 5% PVP (as binder) formulation, the tablet hardness is less than about 3 Kp with a 30 minute humidification treatment, regardless the length of the drying time. Extending the humidification time to about 60 minutes will typically result in a tablet hardness increase to about 4.0 kp to about 5.0 Kp, regardless the length of the drying time. Further extending the humidification time to about 120 minutes will typically result in a tablet hardness increase to about 5 Kp to about 7 Kp to about 12 kp, regardless the length of the drying time. Means to measure tablet hardness is described below.

The invention provides tablets that, after drying, have a hardness in the range of about 0.5 kilopounds (kp) to about 12.0 Kp. In a preferred embodiment, the tablet hardness is in the range of about 4 kp to about 7 kp, most preferably greater than about 6.0 kp.

3. MEASURING TABLET PROPERTIES

The manufacturing methods of the invention produce a novel tablet capable of rapidly disintegrating in a body cavity, as when placed onto a mucous membrane, as in the buccal space, sublingually, intravaginally, intrarectally, and the like, yet hard enough to withstand packaging, shipping and patient handling. The superior qualities (physical properties) of the tablet of the invention can be measured, and such measurements can be used, e.g., for quality control, to compare to tablets manufactured by other processes. Physical properties can be measured using a variety of conventional assays and tests well described in the patent, pharmaceutical and scientific literature. See, e.g., Kopp (1989) *J. Pharm. Pharmacol.* 41:79–82. A few exemplary tests are set forth below, including means to measure tablet hardness, friability, disintegration time, dissolution time, wetting time, and porosity.

1. Tablet Hardness: "Crushing," or "Tensile" Strength

Tablet hardness is physical strength measurement of the tablet. The resistance of a tablet to chipping, abrasion, or breakage under conditions of storage, transportation and handling before usage depends on its hardness, or "crushing strength." The tablet "crushing" or "tensile" strength is defined as the force required to break a tablet by compression in the radial direction. It is typically measured using one of the many commonly available tablet hardness testers. For example, "Stokes" and "Monsanto" hardness testers measure the force required to break the tablet when the force generated by a coil spring is applied diametrically to the tablet. A "Strong-Cobb" hardness tester also measures the diametrically applied force required to break a tablet, the force applied by an air pump forcing a plunger against the tablet placed on an anvil. Electrically operated hardness testers, such as the Schleuniger apparatus (also known as a "Heberlein") can be used. See also, TS-50N, Okada Seiko Co., Japan; Bi (1996) *Chem. Pharm. Bull.* (Tokyo) 44:2121–2127.

2. Friability

Tablet friability is a physical strength measurement of a tablet, and is defined as the ability of the compressed tablet to resist abrasion and attrition. It is typically measured by turning tablets in a rotating vessel and determining weight loss (see De Jong (1987) *Pharm Weekbl* (Sci) 9:24–28). These rotating devices are called "friabilators." The friabilator provides frictional abrasion to the tablet sample and is used to measure the resistance to abrasion or attrition of tablets. The loss of weight is measured after a fixed number of revolutions of a drum rotating at a controlled rate.

Friabilator apparatus typically use a 285 mm drum of transparent synthetic polymer with polished internal surfaces. One side of the drum is removable. The tablets are tumbled at each turn of the drum by a curved projection that extends from the middle of the drum to the outer wall. The drum is attached to the horizontal axis of a device that rotates at about 25 to 30 rpm. Thus, at each turn, the tablets roll or slide and fall onto the drum wall or onto each other. Many such apparatus are commonly available, e.g., the Roche type friabilator (Van Kel Industries, Inc., Edison, N.J.); a Erweka Friability Apparatus (Erweka Instruments, Milford, Conn.) (Bi (1996) supra, Chowhan (1982) *J. of Pharm. Sci.* 71:1371–1375), and the like.

In one exemplary protocol, the standard United States Pharmacopia (USP) protocol for measuring friability is used. Briefly, the tablets are placed in a friabilator that is a 285 mm drum, about 39 mm in depth, of transparent synthetic polymer. The tablets are "tumbled" at each turn of the drum by a curved projection that extends from the middle of the drum. The drum is rotated for about four minutes at about 25 rpm, resulting in a total of 100 rotations. A minimum of about 20 tablets are used in any test, unless the tablets weigh over 650 mg, in which case only 10 tablets are used. After the allotted time, the tablets are removed from the friabilator, and, with the aid of air pressure or a brush, adhering particles and dust are removed, and remaining tablets are accurately weighed. Percent loss of weight is calculated.

3. In Vivo Disintegration Time

In measuring in vivo disintegration time, the amount of time needed for a tablet to completely disintegrate in a test subject's mouth is measured. The tablet is placed on the subject's tongue; a chronometer is started as soon as the tablet contacts the tongue. The subject in instructed to gently move the tablet against the upper part of the mouth with the tongue. It is emphasized to the subject that this is a gently motion, with no biting of the tablet. Immediately after the last noticeable granule is disintegrated, the chronometer is stopped. This test is repeated with the same subject at least twice, thoroughly rinsing the mouth between tests.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

Composition and Preparation of Rapidly Disintegrating Tablets

The following example details the manufacture of a tablet of the invention possessing rapid disintegration properties.

The general process involves wet granulation of a filler with a binding agent solution to form particles of appropriate size and physical properties. In this example, the filler is mannitol and the spraying binder solution is a mixture of maltose and polyvinylpyrrolidone (PVP), in particular, a PVP with a molecular weight of about thirty thousand daltons, such as Povidone Kollidon® 30 (BASF, Japan). When an active drug component is included, the amount of mannitol is reduced in an amount equal to the amount of active drug being added, thereby maintaining the same total granulation weight. No organic solvents were used in the manufacturing process and the finished tablets have no organic solvent residues.

Mannitol USP is screened through a #20 mesh screen and accurately weighed in a proper container. A 15% maltose/PVP solution was prepared with a maltose:PVP weight ratio of about 9:1. Mannitol is transferred to the fluid bed granulator (Model Versa Glatt GPCG-1) set for top spraying. Spraying of the maltose/PVP solution commenced after the product temperature was greater than (>) about 42° C. The spray rate was gradually increased from 10 g/min to 15 g/min until the entire binder solution was expended. The granulation was maintained at about 30° C. to 40° C. until dry, with a loss on drying at less than about 2 percent (LOD<2.0%). The granulation is discharged from the granulator, sieved through a #20 mesh screen and weighed for calculation of yield.

Separately, the lubricant (magnesium stearate) is sieved through a #20 mesh screen. The dry granulation and magnesium stearate are dry blended to achieve content uniformity (generally but not limited to 5 minute blending time). The blended granulation is then compressed (using a Courtoy Press Model D090) into tablets at 0.4–0.6 kp hardness in a Stokes D3 press.

The resulting tablets are then subjected to a treatment process which involves two steps: 25° C. and 85%RH for 30 minutes (humidification) followed by 40° C. and 30% RH for 30 minutes (drying). The final tablet product can then be packaged or stored in bulk as needed. Characteristic tablets properties are as follows: Hardness: between about 3.0 to 8.0 kp; Friability: less than (<) about 1.0%; In vivo disintegration time: between about 10 to 15 seconds. In vivo disintegration time measured as described above. Hardness and friability by USP standards, as described herein (the Friability tester was Model TA3R, Erweka-Apparatebau-C.M.B.H., and the Hardness tester was Model 6D, Schleuniger Pharmaton).

Example 2

Polyvinylpyrrolidone (PVP) Maintains Tablet Hardness and Decreases the in vivo Disintegration Time of Rapidly Disintegrating Tablets Tablets containing the following ingredients were prepared according to the manufacturing procedure described in Example 1. The weight percentages of the ingredients of the control tablets and PVP-containing tablets of the invention ("PVP tablets") are:

|  | Control Tablets | PVP Tablets |
| --- | --- | --- |
| Mannitol | 94.0% | 94.0% |
| Maltose | 5.0% | 4.5% |
| PVP | — | 0.5% |
| Magnesium stearate | 1.0% | 1.0% |

Mannitol was granulated with an aqueous spraying solution of maltose either with or without polyvinylpyrrolidone (PVP) (as described above). The resulting granulation was dry blended with magnesium stearate and compressed utilizing a conventional tablet press (see above) and subjected to a specific temperature and humidity treatment process identical for both control and PVP tablet formulations (25° C. and 80% RH for 30 minutes followed by 30° C. and 40% RH for 30 minutes).

The hardness and in vivo disintegration times of the resulting tablets were quantitated as described above.

|  | Hardness (kp) | In Vivo Disintegration (sec) |
| --- | --- | --- |
| Control Tablets | 6.0 ± 1.3 (n = 6) | 14 ± 1.7 (n = 6) |
| PVP Tablets | 5.7 ± 0.8 (n = 5) $^{ns}$ | 9 ± 2.4 (n = 5) * |

$^{ns}$ Not statistically different from control tablets
* Statistically different from control tablets at the p <0.01 level This data demonstrates that the inclusion of 0.5% PVP in the formulation resulted in tablets which retain desired physical properties and demonstrate a statistically significant decrease in vivo disintegration time.

Example 3

Polyvinylpyrrolidone Improves the Organoleptic Properties of Rapidly Disintegrating Tablets An important feature of tablets which are design to rapidly disintegrate in the oral cavity is the organoleptic properties, i.e. the taste, feel, and general sensory perception of the disintegrating dosage form. Tablets were prepared as described in Examples 1 and 2, above (including conditions for granulation, compression, humidification, and drying treatment). The weight percentage ingredients for the control tablets and the PVP-containing tablets of the invention were:

|  | Control Tablets | PVP Tablets |
| --- | --- | --- |
| Coated famotidine | 8.7% | 8.7% |
| Mannitol | 84.8% | 84.8% |
| Maltose | 5.0% | 4.5% |
| Peppermint powder | 0.5% | 0.5% |
| PVP | — | 0.5% |
| Calcium stearate | 1.0% | 1.0% |

A volunteer panel was used to evaluate the organoleptic properties of the two formulations. They were asked to evaluate three parameters: smoothness, residues and dryness. "Smoothness" represents how "smooth" a tablet feels upon dissolving in the mouth, i.e., the texture of the tablet as sensed in the mouth (also described as the "creaminess" of the tablet), the presence or lack of a gritty or gummy sensation on the tongue during a "tumbling action" (tumbling the tablet between tongue and palate), the presence or absence of a "tacky" sensation or a "heaviness" feeling. "Residues" represents how consistently a type of tablet dissolves in the mouth, the textural feeling of the tablet in the mouth after disintegration, i.e., the presence or absence of an residual sensation of "particles" remaining in the mouth or a residual "mouthcoating" sensation. "Dryness" represents any "dry feeling" in the mouth during or after a tablet has disintegrated, i.e., the level of moisture content in the mouth during the dissolving process.

| | Number of subjects expressing tablet preference | | | |
| --- | --- | --- | --- | --- |
| Tablet | Smoothness | Residues | Dryness | Overall |
| Control | 3 of 11 | 3 of 11 | 1 of 11 | 4 of 11 |
| PVP | 6 of 11 | 5 of 11 | 4 of 11 | 7 of 11 |
| No difference | 2 of 11 | 3 of 11 | 6 of 11 | — |

This data clearly indicates that the subjects had a preference for the PVP-containing tablets of the invention as compared to control tablets. This indicates that the inclusion of PVP in the formulation of the invention results in a tablet whose physical and organoleptic properties are superior to those found with a non-PVP containing formulation.

Example 4

Rapidly Disintegration Tablets Containing Polyvinylpyrrolidone (PVP) and 10 mg Famotidine as the Active Drug Tablets were prepared as described in Examples 1 and 2, above (including conditions for granulation, compression, humidification, and drying treatment). The weight percentage ingredients for the PVP-containing tablets were:

| Component | Weight (mg) | Weight Percent |
| --- | --- | --- |
| Mannitol | 126.0 | 84.0 |
| Maltose | 6.75 | 4.5 |
| PVP | 0.75 | 0.5 |
| Famotidine | 10.0 | 6.7 |

-continued

| Component | Weight (mg) | Weight Percent |
|---|---|---|
| Magnesium stearate | 0.75 | 0.5 |
| TOTAL | 150.0 | 100.0 |

These tablets demonstrated superior physical and the rapid in vivo disintegration times characteristic of the tablets of the invention: Hardness, between about 4.5 to 4.8 kp, Friability less than or equal to two percent ($\leq 2.0\%$), Disintegration time, about 7 seconds.

Example 5
Rapidly Disintegration Tablets Containing Polyvinylpyrrolidone (PVP) and 80 mg Acetaminophen as the Active Drug Tablets were prepared as described in Examples 1 and 2, above (including conditions for granulation, compression, humidification, and drying treatment). The weight percentage ingredients for the PVP-containing tablets were:

| Component | Weight (mg) | Weight Percent |
|---|---|---|
| Mannitol | 292.0 | 73.0 |
| Maltose | 18.0 | 4.5 |
| PVP | 2.0 | 0.5 |
| Acetaminophen | 80.0 | 20.0 |
| Magnesium stearate | 2.0 | 0.5 |
| TOTAL | 400.0 | 100.0 |

These tablets demonstrated superior physical and the rapid in vivo disintegration times characteristic of the tablets of the invention: Hardness, 4.8±1.2 kp, Friability 1.1±0.2%, Disintegration time, about 14±0.5 seconds.

Example 6
Rapidly Disintegration Tablets Containing Polyvinylpyrrolidone RVP) and 100 mg Ibuprofen as the Active Drug Tablets were prepared as described in Examples 1 and 2, above (including conditions for granulation, compression, humidification, and drying treatment). The weight percentage ingredients for the PVP-containing tablets were:

| Component | Weight (mg) | Weight Percent |
|---|---|---|
| Mannitol | 325.0 | 65.0 |
| Maltose | 22.5 | 4.5 |
| PVP | 2.5 | 0.5 |
| Ibuprofen | 100.0 | 20.0 |
| Magnesium stearate | 2.5 | 0.5 |
| TOTAL | 500.0 | 100.0 |

These tablets demonstrated superior physical properties and the rapid in vivo disintegration times characteristic of the tablets of the invention: Hardness, 5.4±1.3 kp, Disintegration time, about 10±2.5 seconds.

Example 7
Rapidly Disintegration Tablets Containing Polyvinylpyrrolidone (PVP) and 200 mg Ibuprofen as the Active Drug.

Tablets were prepared as described in Examples 1 and 2, above (including conditions for granulation, compression, humidification, and drying treatment). The weight percentage ingredients for the PVP-containing tablets were:

| Component | Weight (mg) | Weight Percent |
|---|---|---|
| Mannitol | 282.0 | 47.0 |
| Maltose | 27.0 | 4.5 |
| PVP | 3.0 | 0.5 |
| Ibuprofen | 200.0 | 20.0 |
| Magnesium stearate | 3.0 | 0.5 |
| TOTAL | 600.0 | 100.0 |

These tablets demonstrated superior physical properties and the rapid in vivo disintegration times characteristic of the tablets of the invention: Hardness, 5.8±1.9 kp, Friability, about 2.7±2.2%, Disintegration time, about 17±3.2 seconds.

Example 8
Variation in Formulation Composition Including Partial Replacement of Mannitol with Maltose or Lactose as the Filler Ingredient Tablets were prepared as described in Examples 1 and 2, above (including conditions for granulation, compression, humidification, and drying treatment). The weight percentage ingredients for the PVP-containing tablets were:

| | Component Weight Percent (%) | | | | |
|---|---|---|---|---|---|
| Component | Tablet A | Tablet B | Tablet C | Tablet D | Tablet E |
| Filler: | | | | | |
| Mannitol | 95.0 | — | — | — | — |
| Mannitol/ maltose | — | 85.0/10.0 | 76.0/19.0 | — | — |
| Mannitol/ lactose | — | — | — | 85.0/10.0 | 76.0/19.0 |
| Maltose | 4.5 | 4.5 | 4.5 | 4.5 | 4.5 |
| PVP | 0.5 | 0.5 | 0.5 | 0.5 | 0.5 |
| Magnesium stearate | 0.5 | 0.5 | 0.5 | 0.5 | 0.5 |

The physical properties and in vivo disintegration times of the tablets were determined (as described above) and are summarized as follows:

| Tablet Formulation (sec) | Hardness (kp) | Friability (%) | Disintegration |
|---|---|---|---|
| A | 5.7 ± 0.8 | 1.7 | 9 ± 2.4 |
| B | 5.4 ± 1.3 | 0.8 ± 0.5 | 16 ± 0.5 |
| C | 3.9 | 1.1 | 15 |
| D | 6.2 ± 0.3 | 0.7 ± 0.1 | 12 ± 1.0 |
| E | 5.5 ± 1.2 | 0.8 ± 0.1 | 12 ± 0.5 |

Inclusion of PVP in the formulation afforded tablets with desired physical properties, including hardness, friability and disintegration, while maintaining the rapid in vivo disintegration properties characteristic of the tablets of the invention.

Example 9
Effect of Polyvinylpyrrolidone as Sole Tablet Binder: Improvement in Tablet Hardness Under Modified Treatment Conditions.

Tablets were prepared as described in Examples 1 and 2, above (including conditions for granulation, compression, humidification, and drying treatment). The weight percentage ingredients for the PVP-containing tablets were: Mannitol 94.5%, PVP 5.0%, Magnesium stearate 0.5%.

The tablets, prepared according to the above formula by methods described in Examples 1 and 2 through the compression step, were then treated under three different conditions as indicated in the following table. The modified treatment regimen, which utilized longer times for both the humidification and drying steps, afforded a significant increase in tablet hardness while maintaining comparable in vivo disintegration times (comparable to disintegration times seen with 0.5% PVP and 4.5% maltose, as described above).

| Humidification Time (min at 25° C./85% RH) | Drying Time (min at 40° C./ 30% RH) | Hardness in kp | Disintegration Time (Seconds) |
|---|---|---|---|
| 30 | 30 | ~3 | 14 |
| 60 | 30–120 | 4–5 | 20 |
| 120 | 30–120 | 5–7 | 21 |

These data demonstrate that when 5% PVP is used as the only binder ingredient in the tablet (i.e., as a total replacement for maltose in the binder spray solution), and the manufacturing process uses increased humidification times (from between about 30 minutes to about 120 minutes), tablets with significantly superior hardness were produced without compromising in vivo disintegration times.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A process for producing a pharmaceutical tablet, comprising the following steps:
    (a) granulating a formulation comprising a water soluble polyvinylpyrrolidone and at least one active ingredient together, wherein no organic solvents are included in the formulation, and wherein a saccharide of low moldability is included in the formulation;
    (b) compressing the product of the granulation into a tablet form;
    (c) humidifying the tablet by exposing the product of step (b) to an aerated environment at least about 50% to 100% relative humidity; and
    (d) drying the tablet, wherein the hardness of the tablet is between about 0.5 kilopounds to about 12.0 kilopounds, and further wherein the tablet has an in vivo disintegration time of about 1 second to about 40 seconds, and further wherein the tablet comprises an effective amount of the polyvinylpyrrolidone to achieve said in vivo disintegration time and said hardness factor.

2. The process of claim 1, wherein the polyvinylpyrrolidone has a molecular weight of about thirty thousand daltons.

3. The process of claim 1, wherein the polyvinylpyrrolidone is at about 5% of the dry weight of the formulation.

4. The process of claim 1, wherein the polyvinylpyrrolidone is selected from the group consisting of N-vinyl pyrrolidone, 3-methyl N-vinylpyrrolidone, N-vinyl amide pyrrolidone, N-vinyl acetate pyrrolidone, vinylpyrrolidone-vinyl acetate copolymer, and acrylamide- vinylpyrrolidone co-polymer.

5. The process of claim 1, wherein in step (a) the formulation further comprises at least one lubricant.

6. The process of claim 5, wherein the lubricant is in the range of about 0.5% to about 1.0% of the dry weight of the formulation.

7. The process of claim 5, wherein the lubricant in the formulation is magnesium stearate or calcium stearate.

8. The process of claim 5, wherein the sarccharide of low moldability in the formulation is in the range of about 80 to about 98% of the dry weight of the formulation.

9. The process of claim 8, wherein the sacroharide of low moldabiit in the formulation is in the range of about 95% of the dry weight of the formulation.

10. The process of claim 5, wherein the sacchride of low moldability in the formulation is mannitol.

11. The process of claim 1, wherein in step (a) the temperature during granulation ranges from about 10° C. to 70° C.

12. The process of claim 1, wherein in step (b) the compression is by press molding.

13. The process of claim 1, wherein in step (b) the compression produces a tablet with a hardness of about 0.3 to about 6.0 kilopounds.

14. The process of claim 1, wherein in step (c) the humidification is at about 85% relative humidity.

15. The process of claim 1, wherein in step (c) the temperature is at about 25° C.

16. The process of claim 1, wherein in step (c) the humidification step lasts for about 30 minutes.

17. The process of claim 1, wherein in step (c) the humidification step lasts for about 60 minutes.

18. The process of claim 7, wherein the hardness of the dried tablet is about 4 kilopounds to about 5 kilopounds.

19. The process of claim 1, wherein in step (c) the humidification step lasts for about 120 minutes.

20. The process of claim 9, wherein the hardness of the dried tablet is about 5 kilopounds to about 12 kilopounds.

21. The process of claim 20, wherein the hardness of the dried tablet is about 7 kilopounds.

22. The process of claim 1, wherein step (d) occurs at a higher temperature and lower relative humidity than that of step (c).

23. The process of claim 1, wherein step (d) occurs at a temperature of about 40° C.

24. The process of claim 1, wherein step (d) occurs at a relative humidity of about 30%.

* * * * *

UNITED STATES PATENT AND TRADEMARK OFFICE
CERTIFICATE OF CORRECTION

PATENT NO. : 6,465,009 B1  Page 1 of 1
DATED : October 15, 2002
INVENTOR(S) : Fang-yu Liu et al.

It is certified that error appears in the above-identified patent and that said Letters Patent is hereby corrected as shown below:

<u>Title page,</u>
Item [73], Assignee, should read as follows:
-- Yamanouchi Pharmaceutical Co., Ltd., Tokyo, (JP) and Yamanouchi Pharma Technologies, Inc., Norman, OK (USA) --.

Signed and Sealed this

Twenty-third Day of May, 2006

JON W. DUDAS
*Director of the United States Patent and Trademark Office*